United States Patent [19]

Hamill et al.

[11] 3,968,204

[45] July 6, 1976

[54] ANTIBIOTIC A-2315

[75] Inventors: Robert L. Hamill, New Ross; William Max Stark, Indianapolis, both of Ind.

[73] Assignee: Eli Lilly and Company, Indianapolis, Ind.

[22] Filed: Apr. 28, 1975

[21] Appl. No.: 572,050

Related U.S. Application Data

[60] Division of Ser. No. 466,327, May 2, 1974, which is a continuation-in-part of Ser. No. 276,546, July 31, 1972, abandoned.

[52] U.S. Cl. .............................................. 424/121
[51] Int. Cl.$^2$ ........................................ A61K 35/00
[58] Field of Search .................................. 424/121

*Primary Examiner*—Jerome D. Goldberg
*Attorney, Agent, or Firm*—Nancy J. Harrison; Everet F. Smith

[57] ABSTRACT

Antibiotic A-2315 mixture, comprising microbiologically active, structurally related factors A, B, and C, produced by culturing *Actinoplanes philippinensis* NRRL 5462 under submerged aerobic fermentation conditions. Individual factors A, B, and C are separated and isolated by chromatographic procedures. The A-2315 antibiotics are useful in controlling the growth of cariogenic organisms, in promoting the growth of chickens, and in increasing feed-utilization efficiency in ruminants.

2 Claims, 3 Drawing Figures

ANTIBIOTIC A-2315

CROSS-REFERENCE TO RELATED APPLICATION

This is a division of copending application Ser. No. 466,327, filed May 2, 1974, which is in turn a continuation-in-part of application Ser. No. 276,546, filed July 31, 1972, now abandoned.

SUMMARY OF THE INVENTION

This invention relates to novel antibiotic substances and to a process for their production. In particular, this invention relates to neutral, nitrogenous antibiotic factors arbitrarily designated herein as antibiotic A-2315 factors A, B, and C.

The A-2315 antibiotics are produced by culturing the newly characterized *Actinoplanes philippinensis* NRRL 5462 under submerged aerobic fermentation conditions until a substantial amount of antibiotic activity has been produced. The antibiotics are isolated from the filtered fermentation broth as amorphous solids, preferably by extraction with an organic solvent. The antibiotics are further purified and separated into individual factors by column chromatography over activated alumina or silica gel. The A-2315 antibiotics are useful antibacterial agents, particularly against gram-positive streptococci. In one aspect, the A-2315 antibiotics are effective in the inhibition of organisms responsible for dental caries and for periodontal disease. The A-2315 antibiotics also promote growth when incorporated in the diet of poultry, are plant-fungicidal agents and increase feed-utilization efficiency in ruminants.

DESCRIPTION OF THE DRAWINGS

The infrared absorption spectra of the A-2315 antibiotic factors are presented in the drawings as follows.

DETAILED DESCRIPTION OF THE INVENTION

The antibiotic A-2315 factors of the present invention are structurally related to each other. These factors are coproduced during the fermentation and are obtained as a mixture. The factors are separated from each other and isolated as individual compounds as hereinafter described.

Under the conditions employed thus far, cultures of *Actinoplanes philippinensis* NRRL 5462 produce antibiotic A-2315 factor A as the predominant factor. Although the ratio of factors varies as fermentation conditions vary, in general the characterized factors are present in the following amounts (percent of total recovered antibiotic activity):

| factor A | 75–94% |
| factor B | 1–10% |
| factor C | 5–15% |

The following paragraphs describe the physical and spectral properties of the A-2315 factors which have thus far been characterized.

A-2315 FACTOR A

Antibiotic A-2315 factor A is a white, amorphous solid, having a molecular weight of 503.2638, as determined by mass spectrometry, and an elemental analysis as follows: 61.51 percent carbon, 7.51 percent hydrogen, 8.69 percent nitrogen, and 21.53 percent oxygen. Based on elemental analysis and molecular weight, an empirical formula of $C_{26}H_{37}N_3O_7$ is assigned to factor A. Electrometric titration of factor A in 66 percent dimethylformamide in water did not indicate the presence of titratable groups. The specific rotation of A-2315 factor A is $-132°$ when determined at a temperature of 27°C. in methanol in which the concentration of the antibiotic is 0.375 percent on a weight per volume basis.

Figure 1:
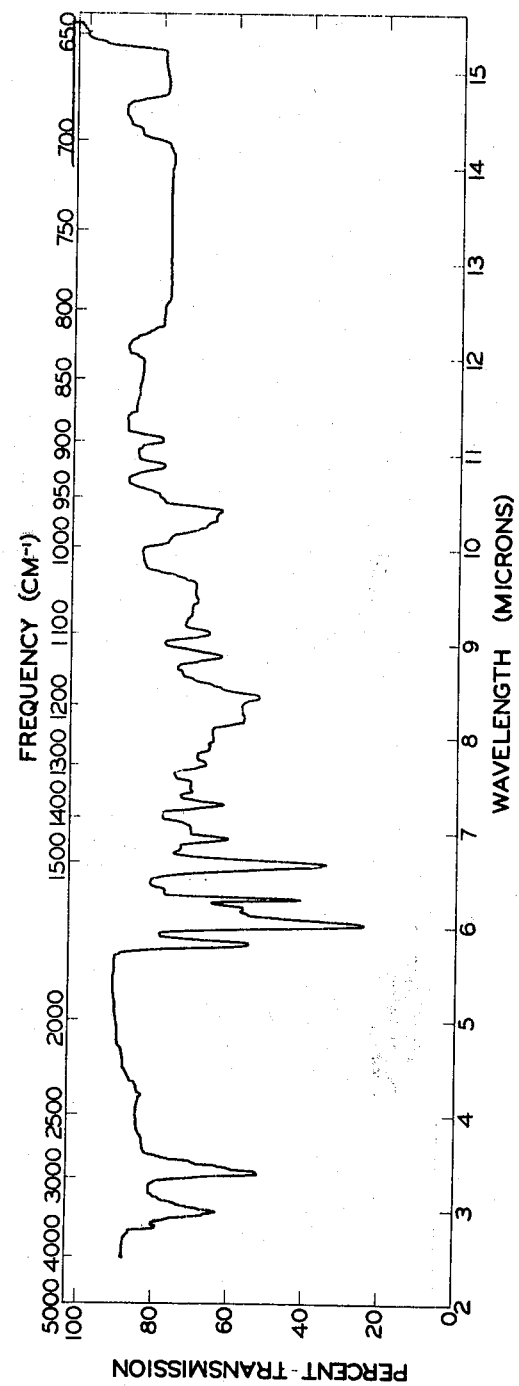
FIG. 1 — A-2315 factor A

The infrared absorption curve of A-2315 factor A in chloroform is shown in the accompanying drawing as FIG. 1. The following distinguishable absorption maxima are observed ($w$ = weak; $m$ = medium; $s$ = strong): 2.81 ($w$), 2.99 ($w-m$), 3.38 ($m$), 5.82 ($m$), 6.02 ($s$), 6.20 ($w$), 6.30 ($m$), 6.40 ($w$), 6.66 ($m-s$), 6.82 ($w$), 6.94 ($w-m$), 7.05 ($w$), 7.30 ($w-m$), 7.71 ($w$), 8.88 ($w-m$), 9.11 ($w-m$), 10.41 ($m$), 10.89 ($w-m$), 11.14 ($w-m$) microns.

The ultraviolet absorption spectrum of A-2315 factor A in 95 percent ethanol shows an absorption maximum at 214 m$\mu$ ($\epsilon$ 40,200) with an absorptivity value ($E_1$ $_{cm}^{1\%}$) of 799.

Antibiotic A-2315 factor A is soluble in methanol, ethanol, higher alcohols, chloroform and most organic solvents, but is only slightly soluble in water.

When subjected to amino-acid analysis, A-2315 factor A releases a large amount of alanine. Factor A contains two hydroxyl groups and is capable of forming ester derivatives in a conventional manner, for example, by acetylation with acetic anhydride in pyridine. These ester derivatives are also useful as antibiotics.

Based upon observed physical data and upon structure elucidation studies, a proposed tentative structure for A-2315 factor A can be devised. The structure has not been determined wth certitude, however; and it is to be understood that the structure presented herein represents merely a working hypothesis. The following structure is postulated for antibiotic A-2315 factor A:

I.

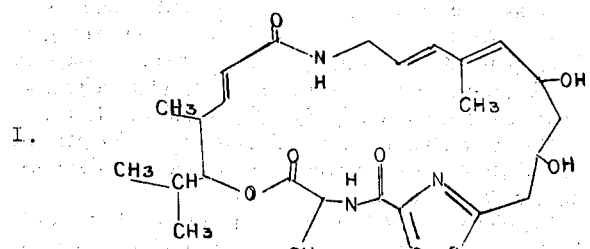

A-2315 FACTOR B

Antibiotic A-2315 factor B is a white, amorphous solid, having a molecular weight of 501, as determined by mass spectrometry, and an elemental analysis as follows: 61.81 percent carbon, 7.02 percent hydrogen, 8.81 percent nitrogen, and 21.42 percent oxygen. Based on elemental analysis and molecular weight, as empirical formula of $C_{26}H_{35}N_3O_7$ is assigned to factor B. Electrometric titration of factor B in 66 percent dimethylformamide in water did not indicate the presence of titratable groups.

Figure 2:
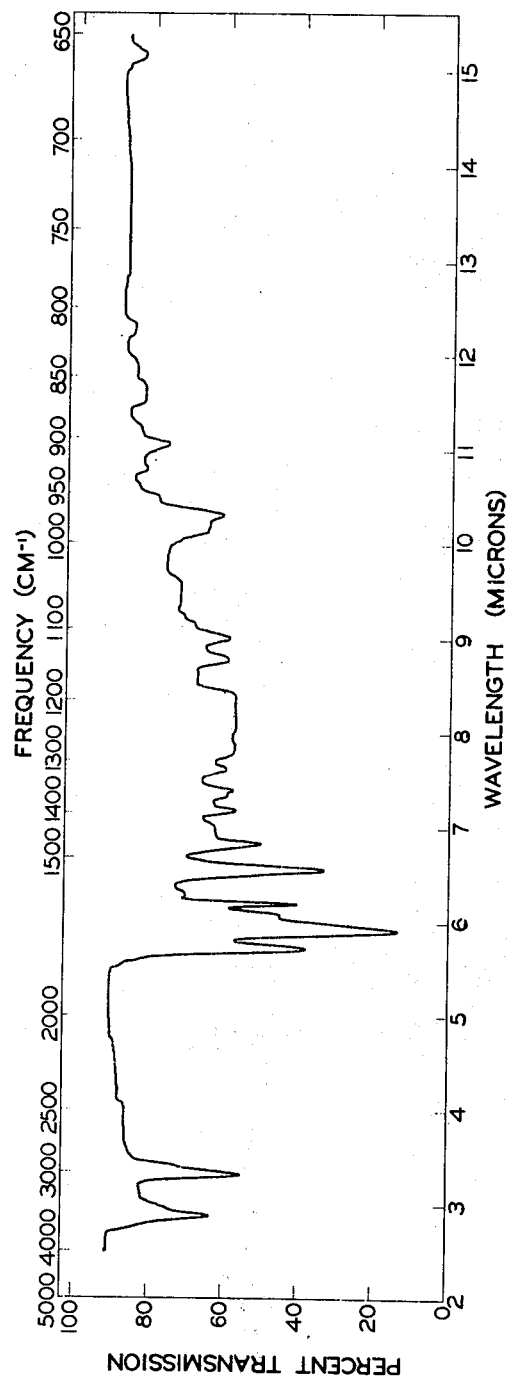
FIG. 2 — A-2315 factor B

The infrared absorption spectrum of A-2315 factor B in chloroform is shown in the accompanying drawings as FIG. 2. The following distinguishable absorption maxima are observed ($w$ = weak) 2.89, 3.31, 5.71, 5.92, 6.19, 6.55, 6.82, 7.19 (w), 7.39 (w), 7.60 (w), 8.78 (w), 9.0 (w), 10.30, 11.05 (w) microns.

The ultraviolet absorption spectrum of A-2315 factor B shows an absorption maximum at 213 m$\mu$ ($\epsilon$ 33,110) with an absorptivity value ($E_{1\ cm}^{1\%}$) of 661 in both neutral and acidic 95 percent ethanol. In basic ethanol, an absorption maximum appears at 298 m$\mu$ ($\epsilon$ 10,456) of forming an ester derivative in a conventional manner, for example, by acetylation with acetic anhydride in pyridine. Such an ester derivative is also useful as an antibiotic.

In the paper chromatography systems indicated below, using *Sarcina lutea* as a detection organism, the A-2315 factors have the following Rf values:

| Solvent System | Rf Value Factor A | Factor B | Factor C |
|---|---|---|---|
| Methyl ethyl ketone (MEK): benzene: water (1:5:1) upper layer | 0.19 | 0.37 | 0.60 |
| Butanol saturated with water | 0.91 | 0.91 | 0.91 |
| Butanol saturated with water plus 2% p-toluenesulfonic acid (p-TSA) | 0.91 | 0.91 | 0.91 |
| Methyl isobutyl ketone (MIBK) saturated with water | 0.56 | 0.64 | 0.71 |
| MIBK saturated with water plus 2% p-TSA | 0.60 | 0.66 | 0.74 |
| Water:methanol:acetone (12:3:1), adjusted to pH 10.5 with NH$_4$OH and then lowered to pH 7.5 with H$_3$PO$_4$ | 0.83 | 0.78 | 0.72 |
| 1% MIBK, 0.5% NH$_4$OH in water | 0.75 | 0.64 | 0.57 |
| 17.4 g. K$_2$HPO$_4$, 30 ml. ethanol per liter of water | 0.72 | 0.65 | 0.53 |
| 7% NaCl plus 2.5% MEK in water | 0.65 | 0.55 | 0.46 |
| Propanol:water (1:9) | 0.84 | 0.81 | 0.78 |
| Butanol:ethanol:water (13.5:15:150) | 0.90 | 0.85 | 0.80 |
| NH$_4$Cl (12.5g); NaCl (35g), dioxane (25ml) and MEK (12.5ml) per liter of water, adjusted to pH 5.7 with dilute NH$_4$OH | 0.69 | 0.59 | 0.51 | with an $E_{1\ cm}^{1\%}$ of 209.

Antibiotic A-2315 factor B is soluble in methanol, ethanol, higher alcohols, chloroform and most organic solvents, but is only slightly soluble in water.

When subjected to amino-acid analysis, A-2315 factor B releases a large amount of alanine. Factor B contains at least one hydroxyl group which is capable of forming an ester derivative in a conventional manner, for example, by acetylation with acetic anhydride in pyridine. Such an ester derivative is also useful as an antibiotic.

A-2315 FACTOR C

Antibiotic A-2315 factor C is a white, amorphous solid, having a molecular weight of 487, as determined by mass spectrometry, and an elemental analysis as follows: 61.04 percent carbon, 7.00 percent hydrogen, 7.96 percent nitrogen, and 22.61 percent oxygen. Based on elemental analysis and molecular weight, an empirical formula of $C_{25}H_{33}N_3O_7$ is assigned to factor C. Electrometric titration of factor C in 66 percent dimethylformamide in water did not indicate the presence of titratable groups.

Figure 3:
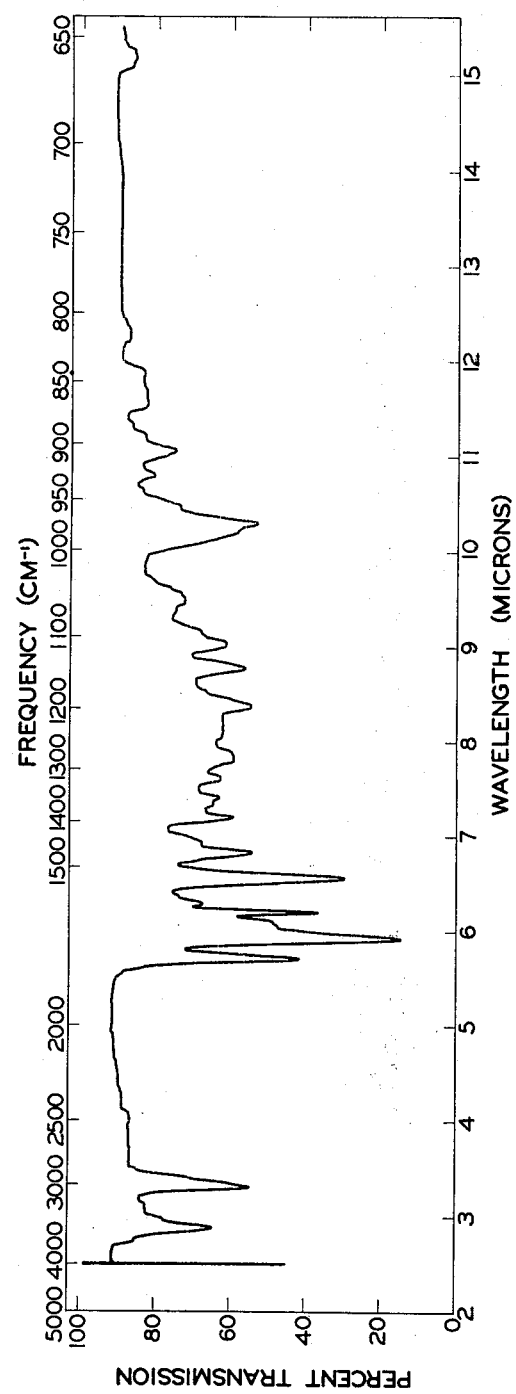
FIG. 3 — A-2315 factor C

The infrared absorption spectrum of A-2315 factor C in chloroform is shown in the accompanying drawing as FIG. 3. The following distinguishable absorption maxima are observed (w = weak): 2.88, 3.30, 5.70, 5.92, 6.18, 6.55, 6.82, 7.18 (w), 7.40 (w), 7.60 (w), 7.80 (w), 8.35, 8.75, 9.0 (w), 9.45 (w), 10.28, 10.78 (w), 11.04 microns.

The ultraviolet absorption spectrum of A-2315 factor C shows absorption maxima at 212 m$\mu$ ($\epsilon$ 34,011) with an absorptivity value ($E_{1\ cm}^{1\%}$) of 698 and 278 m$\mu$ ($\epsilon$ 7,014) with an $E_{1\ cm}^{1\%}$ of 144 in neutral, acidic and basic 95% ethanol.

Antibiotic A-2315 factor C is soluble in methanol, ethanol, higher alcohols, chloroform and most organic solvents, but is only slightly soluble in water.

When subjected to amino-acid analysis, A-2315 factor C releases a large amount of alanine. Factor C contains at least one hydroxyl group which is capable of forming an ester derivative in a conventional manner, for example, by acetylation with acetic anhydride in pyridine. Such an ester derivative is also useful as an antibiotic.

Thin-layer chromatography on silica gel, using a chloroform-methanol (9:1) solvent system and *Sarcina lutea* as a detection organism, gives good separation of the A-2315 factors as follows:

|  | Rf Value |
|---|---|
| Factor A | 0.23 |
| Factor B | 0.38 |
| Factor C | 0.47 |

The A-2315 antibiotics inhibit the growth of certain microorganisms. The levels at which the A-2315 antibiotics inhibit the growth of organisms were determined using various testing procedures.

DISC-PLATE SCREENING PROCEDURE

Agar plates, inoculated with the test organism, are used; 6 mm. discs (0.02 ml. capacity) are saturated from log 2 dilutions of the antibiotic solution. Disc content is 1/50 of the concentration of the solution used, i.e. disc content of 30 $\mu$g. obtained from a solution of 1500 $\mu$g./ml concentration. The minimal inhibitory concentration (MIC) of test compounds is reported.

AGAR-DILUTED SCREENING PROCEDURE

The agar-dilution procedure described by the International Collaborative Study (ICS) group is used to determine MIC values.

The results obtained from tests of antibiotic A-2315 factor A are given in Table I.

TABLE I

| ACTIVITY OF A-2315 FACTOR A | | |
|---|---|---|
| Test Organism | MIC ($\mu$g/disc)[1] | MIC ($\mu$g/ml)[2] |
| *Staphylococcus aureus* 3055* | 0.025 | 6.25 |
| *Staphylococcus aureus* 3130*** | 0.2 | |
| *Staphylococcus aureus* 3074*** | 0.4 | 1.56 |
| *Mycobacterium avium* | 3.13 | |
| *Streptococcus pyogenes* | 0.012 | |
| *Bacillus subtilis* | 50. | |
| *Sarcina lutea* | 0.008 | |
| *Proteus sp.* | 100. | |
| *Escherichia coli* | 12.5 | |

TABLE I-continued

ACTIVITY OF A-2315 FACTOR A

| Test Organism | MIC (μg/disc)[1] | MIC (μg/ml)[2] |
|---|---|---|
| Salmonella typhimurium | 12.5 | >100.00 |
| Salmonella typhosa | 12.5 | >100.00 |
| Shigella flexneri | 1.56 | |
| Klebsiella pneumoniae K1 | 12.5 | |
| Klebsiella pneumoniae KA14 | 50.0 | |
| Candida albicans | 100.0 | |
| Streptococcus faecalis | | 1.56 |
| Erwinia amylovora | | 50.00 |

*benzylpenicillin-susceptible
**benzylpenicillin-resistant
***benzylpenicillin-resistant, methicillin-resistant
[1]Disc-Plate Method
[2]Agar-Dilution Method The results obtained from agar-dilution tests of antibiotic A-2315 factors B and C are given in Table II.

TABLE II

ACTIVITY OF A-2315 FACTORS B AND C

| Test Organism | MIC (μg/ml) Factor B | Factor C |
|---|---|---|
| Staphylococcus aureus 3055* | 1.56 | 12.5 |
| Staphylococcus aureus 3074** | 1.56 | 6.25 |
| Streptococcus faecalis | 1.56 | 25.0 |
| Bordetella bronchiseptica | 100.0 | >100.0 |
| Erwinia amylovora | 25.0 | >100.0 |
| Aspergillus flavus | 50.0 | >100.0 |

*benzylpenicillin-susceptible
**benzylpenicillin-resistant

The A-2315 antibiotics are also active against anaerobic bacteria. In one aspect of this activity, the A-2315 antibiotics are active against *Treponema hyodysenteriae*, a cause of swine dysentery. The minimal concentrations of A-2315 factors which inhibit this organism, as determined by the agar-dilution method, are as follows:

| | MIC (μg/ml) |
|---|---|
| Factor A | <0.195 |
| Factor B | 1.56 |
| Factor C | 12.5 |

Further tests against other anaerobic organisms, are summarized in Table III.

TABLE III

ACTIVITY OF A-2315 FACTORS — ANAEROBIC BACTERIA

| Test Organism | MIC (μg/ml) Factor A | Factor B | Factor C |
|---|---|---|---|
| Actinomyces bovis | 16.0 | 1.0 | >128.0 |
| Clostridium inocuum | 32.0 | 64.0 | >128.0 |
| Clostridium perfringens | 32.0 | 64.0 | >128.0 |
| Clostridium ramosum | 8.0 | 64.0 | 64.0 |
| Clostridium septicum | 32.0 | 8.0 | >128.0 |
| Eubacterium aerofaciens | 16.0 | 4.0 | >128.0 |
| Peptococcus anaerobius | 2.0 | 1.0 | 32.0 |
| Peptostreptococcus intermedius | 8.0 | 16.0 | >128.0 |
| Propionibacterium acnes | 8.0 | 1.0 | 64.0 |
| Bacteriodes fragilis ssp. vulgates | 64.0 | 16.0 | 16.0 |
| Bacteriodes fragilis ssp. fragilis | 128.0 | 32.0 | 64.0 |
| Bacteriodes fragilis ssp. thetaotamicron | 128.0 | 16.0 | 16.0 |
| Fusobacterium nucleatum | 128.0 | 8.0 | 128.0 |
| Fusobacterium necrophorum | 16.0 | 8.0 | 128.0 |
| Veillonella alcalescens | 16.0 | 8.0 | 16.0 |

Antibiotic A-2315 factors A and B, when given by subcutaneous injection to mice, have shown in vivo antimicrobial action against experimental bacterial infections. When two doses each of A-2315 factors were administered to mice in illustrative infections, the $ED_{50}$ values [effective dose in mg/kg to protect 50 percent of the test animals; see Warren Wick, et al., J. Bacteriol. 81, 233–235 (1961)] are shown in Table IV:

TABLE IV

| | Test I[1] Factor A | Factor A | Test II[2] Factor B | Factor C |
|---|---|---|---|---|
| Staphylococcus aureus 3055 | 90 | 45.7 | 31.4 | >83.0 |
| Streptococcus pyogenes | 83 | 27.4 | 19.1 | >83.0 |

[1]Infecting challenges:  S. aureus 4000 × $LD_{50}$(ip)
S. pyogenes 10,000 × $LD_{50}$ (ip)

[2]Infecting challenges: S. aureus 3.16 × $LD_{50}$(ip)
S. pyogenes 3225 × $LD_{50}$(ip)

The acute toxicity of antibiotic A-2315 factor A, administered either orally or subcutaneously to mice and expressed as $LD_0$, is greater than 500 mg./kg. The acute toxicities of the A-2315 factors, administered intraperitoneally to mice and expressed as $LD_{50}$ are as follows:

| Factor A | >400 mg/kg |
|---|---|
| Factor B | >300 mg/kg |
| Factor C | >300 mg/kg |

Another useful property of the A-2315 antibiotics is activity against *Mycoplasma gallisepticum*, an organism pathogenic for poultry. Of particular interest is the activity of the A-2315 antibiotics against strains of this organism that are resistant to tylosin. The minimal inhibitory concentrations of A-2315 factor A, as determined by in vitro broth-dilution studies, are summarized in Table V below:

TABLE V

SENSITIVITY OF MYCOPLASMA GALLISEPTICUM (MG) TO A-2315 FACTOR A

| MG Isolate | MIC (μg./ml.) |
|---|---|
| 34159 (tylosin resistant) | 0.195 |
| 41313 (tylosin resistant) | 0.78 |
| 42854 (tylosin resistant) | 0.195 |
| 43480 (tylosin resistant) | <0.097 |
| 38502 (tylosin sensitive) | <0.097 |

Further evaluation of A-2315 factor A in chickens infected with *Mycoplasma gallisepticum* indicated some weight advantage and lowered incidence of air-sac lesions in surviving chickens. The antibiotic factor was prepared in polyethylene glycol 200 and injected subcutaneously in the neck. No signs of toxicity were seen, except for slight hemorrhage in the neck area in some of the treated chicks that died early. Results of this test are summarized in Table VI.

TABLE VI

ACTIVITY OF A-2315 FACTOR A IN EMBRYO CHICKS INFECTED WITH MYCOPLASMA GALLISEPTICUM

| Treatment Groups | Dead Chicks No. Died No. in Group | Air-Sac Lesions | Average Weight | Survivors[a] Air-Sac Lesions | MG Antibody |
|---|---|---|---|---|---|
| Infected Controls | 13/20 | 11/13[b] | 100 gm. | 7/7 | 7/7 |
| Normal Controls | 0/20 | — | 214 gm. | 0/20 | 0/20 |
| A-2315 (3 mg./chick) | | | | | |

TABLE VI-continued

ACTIVITY OF A-2315 FACTOR A IN EMBRYO CHICKS INFECTED WITH MYCOPLASMA GALLISEPTICUM

| Treatment Groups | Dead Chicks No. Died No. in Group | Air-Sac Lesions | Average Weight | Survivors[a] Air-Sac Lesions | MG Antibody |
|---|---|---|---|---|---|
| Factor A | 12/20 | 9/9[c] | 133 gm. | 0/8 | 8/8 |

[a]Data Collected at 14 Days
[b]2/13 not examined due to decomposition
[c]3/9 not examined due to decomposition In one embodiment, therefore, this invention provides agents useful against resistant Mycoplasma in poultry. Protection against Mycoplasma is obtained when an A-2315 antibiotic is administered parenterally or orally to animals in a dosage range of from about 50 to about 5 mg./kg. of animal-body weight. When used to afford either prophylactic or therapeutic protection against this respiratory disease, a suitable concentration of an A-2315 antibiotic is conveniently incorporated into the normal food ration of animals.

In another aspect of the present invention, the A-2315 antibiotics have the ability to inhibit the growth of microorganisms contributing to the development of periodontal disease. In broth-dilution tests, A-2315 factor A inhibits the growth of the cariogenic organism *Streptococcus mutans* at concentrations of 1–2 μg/ml and inhibits the growth of cariogenic filamentous rods at a concentration as low as 0.1 μg/ml.

A solution of antibiotic A-2315 factor A exhibits inhibitory activity against cariogenic organisms as illustrated by the following test system: Tubes of nutrient broth containing 5 percent sucrose are inoculated with cariogenic microorganisms. Narrow glass rods, which extend below the surface of the nutrient broth, are inserted into the tubes. After incubation at 37°C. overnight, a layer of artificial plaque (primarily cells and dextran) forms on the surface of the rods. The rods are then transferred to solutions containing varying concentrations of test compound and are allowed to remain in contact with these solutions for periods of 5, 10, and 15 minutes. After the appropriate time has elapsed, the rods are rinsed by dipping in sterile, deionized water; the rods are then incubated overnight at 37°C. in uninoculated medium containing sucrose and bromothymol blue. Growth is detected by observing the color change of bromothymol blue from green to yellow, due to acid production by the organisms when grown in a sucrose-containing medium. No growth indicates that the test compound has destroyed the organism.

Using this test, a solution of A-2315 factor A at a concentration of 0.1% was effective against a cariogenic *Streptococcus sp.* when the solution was in contact with the plaque-encrusted rods for as little as 5 minutes.

Because of their activity against cariogenic organisms and those organisms implicated in periodontal disease, the A-2315 antibiotics are suitable for incorporation, in inhibitory concentrations, in preparations employed in oral hygiene, such as toothpastes, powders or gels, mouthwashes and the like. In general, preparations containing from about 1 to about 15 percent of an A-2315 antibiotic are useful for the control of cariogenic organisms.

Still another useful property of the A-2315 antibiotics is their ability to improve growth performance in animals. For example, when A-2315 factor A was added to the diet of growing chicks at a level of 45.4 grams/ton, the average weight gain after 10 days was 159 grams, as compared with an average weight gain of 148 grams for the control group. The feed-conversion efficiency (feed/gain) for chickens fed antibiotic A-2315 factor A was 1.44; in contrast, the feed-conversion efficiency for the control group was 1.53.

The ability of the A-2315 antibiotics to stimulate weight gains make them especially useful for this purpose. When used as growth-promoting agents, suitable concentrations of antibiotic are conveniently incorporated into the normal food ration of the animals. The A-2315 antibiotics typically are effective as growth-promoting agents when administered to animals at levels of from about 20 to about 50 grams/ton of feed ration.

The ability to improve feed-utilization efficiency in animals is another important property of the A-2315 antibiotic mixture and of the individual A-2315 factors. For example, the A-2315 antibiotics improve feed utilization in ruminants which have a developed rumen function. Efficiency of feed utilization, in particular efficiency of carbohydrate utilization, is increased by treatments which encourage the animal's rumen flora to produce propionate or butyrate, rather than acetate, compounds. For a more complete discussion of this, see Leng in "Physiology of Digestion and Metabolism in the Ruminant," Phillipson et al., Eds., Oriel Press, Newcastle upon Tyne, England, 1970, pp 408–410; McCullough in *Feedstuffs*, June 19, 1971, page 19; Eskeland et al., in *J. An. Sci. 33*, 282 (1971); and Church et al., in "Digestive Physiology and Nutrition of Ruminants," Vol. 2, pp. 662 and 625 (1971). Some economically important ruminant animals are cattle, sheep and goats.

The ability of the A-2315 antibiotics to increase feed-utilization efficiency in ruminants is illustrated by the following in vitro test of A-2315 factor A:

METHOD

Rumen fluid is obtained from a steer with a surgically-installed fistula opening into the rumen. The steer is maintained on a high-grain ration, the composition of which follows:

| | |
|---|---|
| 69.95% | coarse ground corn |
| 10.00% | ground corncobs |
| 8.00% | soybean meal (50% protein) |
| 5.00% | alfalfa meal |
| 5.00% | molasses |
| 0.60% | urea |
| 0.5% | dicalcium phosphate |
| 0.50% | calcium carbonate |
| 0.30% | salt |
| 0.07% | vitamins A and $D_2$ premix* |
| 0.05% | vitamin E premix** |
| 0.03% | trace mineral premix*** |

*Containing per pound: 2,000,000 I.U. of vitamin A; 227,200 I.U. of vitamin $D_2$ and 385.7 g of soybean feed with 1% oil added
**Corn distillers dried grains with solubles containing 20,000 I.U. of d-alpha-tocopheryl acetate per pound
***Containing manganous oxide, potassium iodide, cobalt carbonate, copper oxide and zinc sulfate A sample of rumen fluid is strained through four layers of cheesecloth, and the filtrate is collected. The particulate matter retained by the cheesecloth is resuspended in enough physiological buffer to return it to the original volume of the rumen fluid, and this suspension is strained again. The buffer used has the following composition:

| g/liter | Ingredient |
|---|---|
| 0.016 | $KH_2HPO_4$ |
| 0.152 | $KH_2PO_4$ |
| 2.260 | $NaHCO_3$ |
| 0.375 | KCl |
| 0.375 | NaCl |
| 0.112 | $MgSO_4$ |
| 0.050 | $CaCl_2.2H_2O$ |
| 0.008 | $FeSO_4.7H_2O$ |
| 0.004 | $MnSO_4.H_2O$ |
| 0.004 | $ZnSO_4.7H_2O$ |
| 0.002 | $CuSO_4.5H_2O$ |
| 0.001 | $CoCl_2.6H_2O$ | as described by Cheng et al. in J. Dairy Sci. 38, 1225-1230, (1955).

The two filtrates are combined and allowed to stand until particulate matter separates to the top. The clear layer is separated, diluted with the same buffer (1:1) and then adjusted to pH 7.0.

The diluted rumen fluid (10 ml) is placed in a 25-ml flask with 40 mg of the above-described feed, an additional 5 mg of soybean protein, and the test compound. Four replicate flasks are used per treatment. Two sets of four control flasks each are also employed. A zero-time control and an incubated 16-hour control are used. All test flasks are incubated for 16 hours at 38°C. After incubation, the pH is measured; and 25 percent metaphosphoric acid (2 ml) is added to each flask. The samples are allowed to settle, and the supernatant is analyzed by gas chromatography for propionate, acetate, butyrate compounds. Active compounds significantly increase propionate production over that of controls.

Test-compound results are statistically compared with control results. The table below shows the ratio of volatile-fatty-acid (VFA) concentrations in treated flasks to concentrations in control flasks.

TABLE VII

Activity of A-2315 Factor A on Ruminal VFA In Vitro

| mcg A-2315-A per ml diluted rumen fluid | Acetate | Butyrate | Propionate | Total VFA |
|---|---|---|---|---|
| 1.0 | 0.95 | 1.04 | 1.15 | 1.05 |
| 0.3 | 0.95 | 1.00 | 1.08 | 1.07 |
| 0.1 | 0.97 | 1.01 | 1.07 | 1.04 |
| 0.0 | 1.00 | 1.00 | 1.00 | 1.00 |

Further evidence of the ability of the A-2315 antibiotics to increase feed-utilization efficiency is provided by an in vivo test of A-2315 factor A in sheep, using a procedure as follows:

METHOD

Two groups of fistulated lambs are allowed slightly more than their normal feed ration for 17 days. Test compound is administered to one group in the feed on a g/ton basis.

The rumen fluids of both groups of animals are sampled on days 3, 7, 10, 14 and 17 of the treatment period.

The fermentation of the ruminal samples is halted by addition of meta-phosphoric acid. Each sample is diluted, centrifuged at 2000 × gravity for 10 minutes; the supernatants are analyzed for volatile fatty acids via the gas chromatographic method of E. S. Erwin, G. J. Marco and E. M. Emery in J. Dairy Sci., 44, 1768 (1966). Molar percentages of ruminal volatile fatty acids are calculated, and the effect is measured as a comparison of the molar percentages of propionic acid in treated animals to those in contemporary controls.

Tables VIII and IX show the results of such a test with A-2315 factor A.

Table VIII

Activity of A-2315 Factor A on Ruminal VFA In Vivo

| Treatment | Amount | No. of Animals | % Propionic Acid Conc. | % Increase Over Control | Increase Relative to Control |
|---|---|---|---|---|---|
| A-2315 Factor A | 15g/ton | 6 | 31.0 | 4.8 | 18.2% |
| Control | | 6 | 26.2 | | |

Table IX

Activity of A-2315 Factor A on Ruminal VFA In Vivo

| Treatment | Amount | No. of Animals | % Butyric Acid Conc. | % Increase over Control | Increase Relative to Control |
|---|---|---|---|---|---|
| A-2315 Factor A | 15 g/ton | 6 | 13.5 | 2.4 | 21.6% |
| Control | | 6 | 11.1 | | |

The A-2315 antibiotic mixture and the individual A-2315 factors typically effect increases in the efficiency of feed utilization when administered to ruminants orally at rates of from about 0.05 to about 7.5 mg/kg/day. Most beneficial results are achieved at rates of from about 0.5 to about 2.5 mg/kg/day.

Preferably, A-2315 antibiotics are administered by mixing them with the animals' feed. The antibiotics can, however, be administered in other ways, for example, tablets, drenches, boluses or capsules. Formulation of these various dosage forms can be accomplished by methods well known in the veterinary pharmaceutical art. Each individual dosage unit should contain an A-2315 antibiotic in a quantity directly related to the proper daily dose for the animal to be treated.

The culture solids, including medium constituents and mycelium, can be used without extraction or separation, but preferably after removal of water, as a source of the A-2315 antibiotics. For example, after production of A-2315 antibiotic activity, the culture medium can be dried by lyophilization; the lyophilized medium can then be mixed directly into feed premix.

The filtered fermentation broth can also be used without extraction, but preferably after removal of water, as a source of A-2315 antibiotics. For example, after production of A-2315 activity, the fermentation broth can be separated from the mycelium by filtration;

the filtered broth can then be dried by lyophilization; and this lyophilized broth can be mixed directly into feed premix.

These methods of supplying the A-2315 antibiotics are advantageous in several ways. A principal advantage is that the active antibiotics are provided at lowered cost. Further, the antibiotics are provided in a form which is in itself nutritionally advantageous to the animals being treated. By using the medium constituents as part of the product, an ecological advantage is provided in that expensive waste removal treatment becomes unnecessary.

In yet another aspect of the invention, the A-2315 antibiotics are useful as plant-fungicidal agents. At concentrations of 400 ppm, for example, antibiotic A-2315 factor A protected bean plants which had been inoculated with bean rust (*Uromyces phaseoli var. typica*) and gave moderate protection to cucumber plants which had been inoculated with anthracnose (*Colletotrichum lagenarium*). Only slight phytotoxicity was observed in either case.

In order to protect plants, a fungicidally-effective amount of an A-2315 antibiotic may be applied in different ways, for example, in the form of liquid sprays or dusting powders, using suitable solvents, carriers, emulsifiers, wetting agents or surface-active agents as needed. Although individual conditions must be considered, an A-2315 antibiotic is typically useful in the control of fungi when administered to plants in amounts of from about 200 to about 500 ppm.

As is apparent from the foregoing properties, the A-2315 antibiotics are useful for suppressing the growth of pathogenic organisms. In addition to the foregoing applications, solutions containing as little as 2 percent of an A-2315 antibiotic are useful for disinfecting glassware, dental and surgical instruments, and surfaces such as walls, floors, and tables in areas where maintenance of sterile conditions is important, for example, in hospitals, food-preparation areas and the like.

The novel antibiotics of this invention are produced by culturing an A-2315-producing strain of an Actinoplanes organism under submerged aerobic conditions in a suitable culture medium until the culture medium contains substantial antibiotic activity. The antibiotics are recovered by employing various isolation and purification procedures commonly used and understood in the art. The individual antibiotic factors are separated by routine chromatographic procedures.

The microorganisms useful for the preparation of the A-2315 antibiotics has been taxonomically characterized as a new strain of *Actinoplanes philippinensis* Couch. The genus Actinoplanes is a member of the Actinoplanaceae, a family of microorganisms of the order Actinomycetales. The Actinoplanaceae family was first described by Couch [*J. Elisha Mitchell Sci. Soc.*, 65, 315–318 (1949); *ibid.*, 66, 87–92 (1950); *Trans. New York Acad. Sci.*, 16, 315–318 (1954); *J. Elisha Mitchell Sci. Soc.*, 71, 148–155 and 269 (1955); "Bergey's Manual of Determinative Bacteriology," Seventh Edition, 825–829 (1957); *J. Elisha Mitchell Sci. Soc.*, 79, 53–70 (1963)].

The methods employed in the taxonomic studies of the A-2315-producing strain of Actinoplanes are similar to those recommended by the International Streptomyces Project along with other supplementary tests commonly used in taxonomy [E. B. Shirling and D. Gottlieb: "Methods for Characterization of Streptomyces Species." *International Bull. Systemic Bacteriol.*, 16, 313–340 (1966)].

MORPHOLOGY

Vegetative Mycelium

The hyphae on synthetic and semisynthetic agar media are at first short, slightly branched, septate and 0.2 to 1.2 $\mu$m. in diameter. After about 2 weeks, the colonies may consist of well-defined masses of vertical hyphae arising from extensive substrate hyphae buried more deeply in the agar medium; or, alternatively, they may consist of slightly mucoid masses of shorter hyphae which obscure the vertical hyphae. In the colonies with a well-defined mass of vertical hyphae, the mycelia form a compact, slightly raised leathery growth. In the colonies with the shorter hyphae, the mycelia form a predominantly dome-shaped growth. No aerial hyphae are produced on any media. Sporangia are produced in large numbers on the surface of the dome-shaped colonies.

Sporangia

Sporangia are formed in abundance on semisynthetic Anio-Henssen agar. They appear after about 2 to 4 weeks of incubation at 17° to 19°C. The sporangia are borne singly on very short sporangiophores (terminal portion of hyphae above the agar surface). The sporangia may be spherical, subspherical or slightly fan-shaped and are relatively small, having diameters of 4 to 10 $\mu$m. The sporangia contain 20 to 40 subspherical sporangiospores which are arranged in one or more indistinct coils in the sporangia. The sporangiospores are approximately 1.0 $\mu$m. in diameter at maturity. Sporangial dehiscense appears to be by the complete or partial disintegration of the sporangium. Ten or 15 minutes after being placed in water, the sporangia begin to swell to a typically spherical shape and then to liberate spores by wall disintegration. The spores are usually not immediately motile, but become actively motile by means of polar flagellae in about 5 minutes.

APPEARANCE ON MEDIA

Czapek Solution Agar

Good growth; a point inoculum produces a colony about 0.75 cm. in diameter in 4 weeks. No aerial hyphae are observed. The colony is generally flattened with a slight central peak. The colony color is a moderate orange. Sporangia are only rarely observed.

Peptone Czapek Solution Agar

Good growth; a point inoculum produces a colony about 1.0 cm. in diameter in 4 weeks. No aerial hyphae are observed. The colony is slightly raised and somewhat convoluted or bumpy. The colony color is a dull red brown to orange brown. No sporangia are produced.

Anio-Henssen Agar

Growth fair; a point inoculum produces a colony about 0.5 cm. in diameter in 4 weeks. No aerial hyphae are observed. The colony is mounded with a round, cruciform or star-shaped central depression or crevasse. The colony color is a dull gray to gray white. Sporangia are formed in large numbers in colonies incubated at 7° to 19°C. and in small numbers on colonies incubated at higher temperatures.

Cultural characteristics on various media are described in Table X. The designations ICP refer to International Streptomyces Project media (Shirling and Gottlieb).

TABLE X

CULTURE CHARACTERISTICS ON VARIOUS MEDIA
(Incubation Temperature 30°C.)

| Medium | Vegetative Mycelium Amount | Reverse Color M P Code* ICNB Name** | Soluble Pigment |
|---|---|---|---|
| Emerson's | 3+ | 13K8; strong yellowish br. | Brown |
| Glycerol Glycine | 4+ | 9L8; strong orange | Slight brown |
| Glucose Asparagine | 3+ | 10F7; moderate orange | None |
| Inorganic salts-starch agar (ICP 4) | 3+ | 12A8; moderate orange | Slight brown |
| Glycerol asparagine agar (ICP 5) | 4+ | 12A9; brownish orange | None |
| Calcium Malate | 2+ | 44B1; reddish gray | Slight Purple |
| Bennett's | 3+ | 12C7; light brown | Slight brown |
| Oatmeal agar (ICP 3) | 2+ | 44B1; reddish gray | None |
| Yeast extract-malt extract agar (ICP 2) | 3+ | 12D7; light brown | None |
| Nutrient | 1-2+ | 12E6; light yellow brown | None |
| Czapek's | 3+ | 11C9; moderate orange | None |
| Yeast Extract | 3+ | 13H7; yellow beige | None |
| Tyrosine | 1+ | No assignment because of poor reverse | None |
| TPO | 2-3+ | 12E7; light brown | Brown |

*Refers to A. Maerz and M. Rea Paul, "A Dictionary of Color,"McGraw-Hill, New York, N.Y.
**"The ISCC-NBS Method of Designating Colors and a Dictionary ofColor Names," National Bureau of Standards Circular 553, U.S.Government Printing Office

CELL WALL CHEMISTRY

*Actinoplanes philippinensis* NRRL 5462 possesses a cell-wall chemistry most similar to *Actinoplanes philippinensis* (Szaniszlo and Gooder, 1967). Automatic amino-acid and amino-sugar analyses of cell-wall residues remaining after 18 hours of hydrolysis with 1 ml of 6 N hydrochloric acid at 100°C. revealed that glucosamine, muramic acid, glycine, alanine and 2,6-diaminopimelic acid (DAP) are present in the walls in large concentrations. 2,6-Diamino-3-hydroxy-pimelic acid (HDAP) is noticeably absent. A comparison of the cell-wall amino acids of *Actinoplanes philippinensis* NRRL 5462 and *A. philippinensis* (Szaniszlo) is presented in Table XI.

TABLE X

| MOLAR RATIOS[a] OF PRINCIPAL CELL-WALL AMINO ACIDS | | | | | |
|---|---|---|---|---|---|
| Organism | Glutamic | Glycine | Alanine | HDAP | DAP |
| A. philippinensis NRRL 5462 | 1.00 | 1.14 | 0.59 | | 1.10 |
| A. philippinensis (Szaniszlo and Gooder | 1.00 | 1.08 | 0.57 | | 1.06 |

[a]Glutamic acid is considered as unity.

Paper-chromatographic analyses of residues remaining after 2 hours of hydrolysis with 2 ml of 2 N sulfuric acid at 100°C. revealed that the monosaccharides glucose, galactose, mannose, arabinose, xylose and rhamnose are present in the cell walls in detectable quantities. These sugars were also found in the cell walls of *A. philippinensis* (Szaniszlo and Gooder).

Based on the foregoing taxonomic description, the A-2315-producing organism has been classified as a novel strain of *Actinoplanes philippinensis* Couch. The culture herein described differs from the published description of that species in that it does not produce sporangia on glucose asparagine agar media; also, slight color differences are observed on three media. These differences indicate the variations in strains, but do not constitute a difference in species.

The Actinoplanes culture useful for the production of the A-2315 antibiotics has been deposited without restriction as to availability and made a part of the stock culture collection of the Agricultural Research Service, Northern Marketing and Nutrition Research Division, U.S. Dept. of Agriculture, Peoria, Illinois 61604, from which it is available to the public under the number NRRL 5462.

As previously noted, *Actinoplanes philippinensis* NRRL 5462 can be grown in a culture medium to produce the A-2315 antibiotics. The culture medium can be any one of a number of media; however, for economy of production, maximum yield, and ease of isolation of the antibiotic, certain culture media are preferred. Thus, for example, glucose is one of the preferred sources of carbohydrate, and soybean meal is one of the preferred nitrogen sources.

Nutrient inorganic salts to be incorporated in the culture medium can include the customary salts capable of yielding sodium, potassium, ammonium, calcium, phosphate, chloride, sulfate, acetate, carbonate, and like ions. Additionally, sources of growth factors such as distiller's solubles and yeast extracts can be included with beneficial results.

As is necessary for the growth and development of other microorganisms, essential trace elements should also be included in the culture medium for growing the Actinoplanes employed in this invention. Such trace elements are commonly supplied as impurities incidental to the addition of the other constituents of the medium.

The initial pH of the culture medium can be varied widely. Prior to inoculation with the organism, however, it is desirable to adjust the pH of the culture medium to between pH 6.5 and 7.3, depending on the particular medium employed. The final pH is determined, at least in part, by the initial pH of the medium, the buffers present in the medium, and the period of time for which the organism is permitted to grow.

Preferably, submerged aerobic fermentation in large tanks is used for the production of substantial quantities of the A-2315 antibiotics. Small quantities of the antibiotic are obtained by shake-flask culture. Because of the time lag in antibiotic production commonly associated with the inoculation of large tanks with the spore form of the organism, it is preferable to use a vegetable inoculum. The vegetative inoculum is prepared by inoculating a small volume of the culture medium with the spore form of mycelial fragments of the organism to obtain a fresh, actively growing culture of the organism. The vegatative inoculum is then transferred to the larger tank. The medium used for the growth of the vegetative inoculum can be the same as that employed for larger fermentations, although other media can be employed.

The A-2315-producing organism can be grown at temperatures between about 20°–40°C. Optimal antibiotic production appears to occur at a temperature of about 30°C.

As is customary in aerobic submerged culture processes, sterile air is blown through the culture medium. For efficient growth of the organism and production of A-2315 antibiotics, the volume of air employed in the tank production preferably is above 0.1 volume of air per minute per volume of culture medium. Optimum growth occurs when the volume of air employed is between 0.2 and 0.8 volumes of air per minute per volume of culture medium.

The production of antibiotics can be followed during the fermentation by testing samples of the broth for antibiotic activity against organisms known to be sensitive to the antibiotics. One assay organism useful in testing the antibiotics of the present invention is *Sarcina lutea*. The bioassay is conveniently performed by paper-disc assay on agar plates.

Generally, maximum antibiotic production occurs within 2 to 6 days in large-tank or shake-flask fermentation. Commonly, maximum antibiotic production is realized within 20 to 96 hours.

The A-2315 antibiotics can be recovered from the culture medium and separated from other substances which may be present by extractive and adsorptive techniques. Extractive processes are preferred for the initial recovery of the A-2315 antibiotics. Chloroform is a suitable solvent for separating the antibiotics from the filtered, basified culture broth, although other commonly used solvents are satisfactory. For further purification of the A-2315 antibiotics and separation into individual antibiotic factors, adsorption and elution procedures using adsorptive materials, such as carbon, polyamide resin, silica gel, Sephadex LH-20, Amberlite XAD polymeric adsorbent and the like, can be advantageously employed.

This invention is further illustrated by the following examples, but is not to be construed as limited thereby.

EXAMPLE 1

A. Shake Flask Fermentation of A-2315

A culture of *Actinoplanes philippinensis* NRRL 5462 was prepared and maintained on an agar slant having the following composition:

| Ingredient | Amount |
| --- | --- |
| Pre-cooked dried oatmeal | 60.0 gm. |
| Debittered dried brewer's yeast | 2.5 gm. |
| $K_2HPO_4$ | 1.0 gm. |
| Czapek's mineral stock* | 5.0 ml. |
| Agar | 25.0 gm. |
| Deionized water | 1100.0 ml. |
| *Czapek's mineral stock has the following composition: | |
| $FeSO_4 \cdot 7H_2O$ (Dissolved in 2 ml. conc. HCl) | 2.0 gm. |
| KCl | 100.0 gm. |
| $MgSO_4 \cdot 7H_2O$ | 100.0 gm. |
| Deionized Water | q.s. to 1 liter |

The pH of the medium was adjusted from about pH 6.2 to pH 7.3 with sodium hydroxide solution. After sterilization by autoclaving at 120°C. for about 30 minutes at 15–20 pounds pressure, the pH of the medium was 6.7.

The slant was inoculated with *Actinoplanes philippinensis* NRRL 5462 and incubated at 30°C. for 10 to 14 days. The culture does not normally sporulate on this medium; it is necessary, therefore, to macerate the mycelial mat with a flattened, sharpened, inoculating needle in order to increase the number of potential growth centers. The macerated mature culture was covered with beef serum and was scraped carefully with a sterile rod to obtain a mycelial suspension. This suspension was divided into six tubes for lyophilization. One of the lyophilized pellets was used to inoculate 50 ml of a vegetative medium having the following composition:

| Ingredient | Amount |
| --- | --- |
| Glucose | 10.0 gm. |
| Potato starch | 30.0 gm. |
| Soybean flour | 20.0 gm. |
| Defatted cottonseed flour | 20.0 gm. |
| $CaCO_3$ | 2.0 gm. |
| Tap water | 1.1 liter |

The inoculated vegetative medium, in a 250 ml flask, was incubated at 30°C. for 72 hours on a rotary shaker operating at 250 rpm.

Ten milliliters of the incubated vegetative medium was used to inoculate 200 ml of a second-stage vegetative growth medium of the same composition as that of the vegetative medium described above. This second-stage medium, in a 1-liter flask, was incubated at 30°C. for 24 hours on a rotary shaker operating at 250 rpm.

B. Tank Fermentation of A-2315

The second-stage vegetative medium (200 ml), prepared as described above, was used to inoculate 25 liters of a sterile production medium of the following composition:

| Ingredient | Percent |
| --- | --- |
| Glucose | 1.0 |
| Potato starch | 4.0 |
| Molasses | 0.5 |
| Soluble meat peptone | 4.0 |
| Enzyme-hydrolyzed casein | 0.4 |
| Soybean flour | 1.0 |
| $MgSO_4$ | 0.3 |
| $CaCO_3$ | 0.2 |
| Antifoam (Dow Corning) | 0.02 |
| Tap water | q.s. 25 liters |

The pH of the medium was 6.4 after sterilization by autoclaving at 120° for 30 minutes at 15–20 pounds pressure. In a 40-liter fermentation tank, the inoculated production medium was allowed to ferment for 4 days at a temperature of 30°C. The fermentation medium was aerated with sterile air at the rate of one-half volume of air per volume of culture medium per minute. The fermentation medium was stirred with conventional agitators at 400 rpm.

C. Isolation of A-2315

The whole fermentation broth from a 25-liter tank grown according to the procedure described in the previous section was filtered, using a filter aid. The filtrate was adjusted to pH 8.5 with 2 N sodium hydroxide, and the resulting solution was extracted with 2/3 volume of chloroform. The chloroform extract was concentrated under vacuum to a low volume and was added slowly with stirring to 20 volumes of petroleum ether (Skellysolve F). The precipitate was separated by filtration and was dried in vacuo to give 3.13 gm. of antibiotic A-2315 mixture.

EXAMPLE II

Separation of A-2315 Factor A

When only a small amount of antibiotic A-2315 mixture is available, only factor A is readily separated. Illustratively, the A-2315 antibiotic mixture, prepared as described in Example I, Section C (3.13 gm.) and dissolved in ethyl acetate (100 ml), was applied to a 2 × 100 cm. column of basic alumina (M. Woelm, Eschwege, Germany). After the column was washed with 300 ml of ethyl acetate, elution with ethyl acetate:ethanol (19:1) gave fractions containing A-2315 factor A activity. These fractions were combined and evaporated to dryness under vacuum. A solution of the residue in a small amount of chloroform was added to 20 volumes of petroleum ether (Skellysolve F) F) to precipitate factor A. The precipitate was separated by filtration and dried under vacuum to give 1.63 gm. of A-2315 factor A.

The elution of activity was monitored by paper-disc agar-plate assay, using *Sarcina lutea* as the test organism, and by thin-layer chromatography (tlc) on silica gel, using ethyl acetate:ethanol (9:1) as the developing system and *Sarcina lutea* as the bioautograph organism; alternatively, iodine vapors or sulfuric acid spray were used for detection purposes.

EXAMPLE III

Separation of A-2315 Factors A, B, and C

When a larger amount of antibiotic A-2315 mixture is available, factors A, B, and C can be separated by one chromatographic procedure. Antibiotic A-2315 mixture (17.4 gm.) prepared as described in Example I was dissolved in warm ethyl acetate (40 ml) and was applied to a 5.6- × 70- cm. column of silica gel (Grace, grade 62), packed in ethyl acetate. The column was eluted as follows:

| Fractions | Amount per Fraction | Solvent |
|---|---|---|
| 1–25 | 100 ml. | ethyl acetate (100%) |
| 26–50 | 100 ml. | ethyl acetate-ethanol (95:5) |
| 51–75 | 100 ml. | ethyl acetate-ethanol (85:15) |
| 76–100 | 100 ml. | ethyl acetate-ethanol (50:50) |

Elution of the column was monitored by tlc as described in Example 2. Another system useful for monitoring separation progress is tlc on silica gel with chloroform-methanol (9:1) solvent. Another useful detection method is spraying first with phosphomolybdic acid, heating to 100°C for a few minutes and then spraying with sulfuric acid.

From the above column, each of the combined fractions was evaporated to dryness under vacuum. The residue thus obtained was dissolved in a small amount of chloroform, and diethyl ether (2 volumes) was added. This mixture was added to hexane (10 volumes), giving a precipitate which was separated by filtration and dried under vacuum to give the individual antibiotic factor.

Using this procedure, combined fractions 39 through 43 gave 610 mg. of factor C; combined fractions 45 through 54 gave 465 mg. of factor B; and combined fractions 58 through 61 gave 4.28 gm. of factor A.

We claim:

1. The method of promoting growth of animals which comprises administering orally to said animals an effective growth-promoting amount of antibiotic A-2315 factor A, said factor being a white amorphous solid having a specific rotation $[\alpha]_D^{27}$ of $-132$ ($c = 0.375$ in methanol); having an approximate elemental composition of 61.51 percent carbon, 7.51 percent hydrogen, 8.69 percent nitrogen, and 21.53 percent oxygen; having an approximate molecular weight of 503 as determined by mass spectrometry; having in chloroform the following distinguishable bands in its infrared absorption spectrum: 2.81, 2.99, 3.38, 5.82, 6.02, 6.20, 6.30, 6.40, 6.66, 6.82, 6.94, 7.05, 7.30, 7.71, 8.88, 9.11, 10.41, 10.89 and 11.14 microns; having in 95% ethanol solution an ultraviolet absorption maximum at 214 m$\mu$ with an absorptivity value ($E_{1cm}^{1\%}$) of approximately 799; being soluble in methanol, ethanol, and chloroform, but being only slightly soluble in water; releasing alanine upon amino-acid analysis; and containing hydroxyl groups which are capable of esterification.

2. A method of increasing the efficiency of feed utilization of ruminant animals having a developed rumen function which comprises administering orally to said animals an effective feed-utilization-increasing amount of antibiotic A-2315 factor A, said factor being a white amorphous solid having a specific rotation $[\alpha]_D^{27}$ of $-132$ ($c = 0.375$ in methanol); having an approximate elemental composition of 61.51 percent carbon, 7.51 percent hydrogen, 8.69 percent nitrogen, and 21.53 percent oxygen; having an approximate molecular weight of 503 as determined by mass spectrometry; having in chloroform the following distinguishable bands in its infrared absorption spectrum: 2.81, 2.99, 3.38, 5.82, 6.02, 6.20, 6.30, 6.40, 6.66, 6.82, 6.94, 7.05, 7.30, 7.71, 8.88, 9.11, 10.41, 10.89 and 11.14 microns; having in 95% ethanol solution an ultraviolet absorption maximum at 214 m$\mu$ with an absorptivity value ($E_{1cm}^{1\%}$) of approximately 799; being soluble in methanol, ethanol, and chloroform, but being only slightly soluble in water; releasing alanine upon amino-acid analysis; and containing hydroxyl groups which are capable of esterification.

* * * * *